(12) United States Patent
Gleason et al.

(10) Patent No.: US 8,378,131 B2
(45) Date of Patent: *Feb. 19, 2013

(54) CO-PRECIPITATED SALTS OF FATTY ACIDS

(75) Inventors: John Gleason, St. Louis, MO (US);
Douglas Jost, St. Louis, MO (US);
Philip H. Merrell, Arnold, MO (US);
Doug Caskey, Overland, MO (US)

(73) Assignee: Jost Chemical Company, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/354,033

(22) Filed: Jan. 19, 2012

(65) Prior Publication Data

US 2012/0116106 A1 May 10, 2012

Related U.S. Application Data

(63) Continuation of application No. 12/731,981, filed on Mar. 25, 2010, now Pat. No. 8,178,707.

(51) Int. Cl.
*C07C 51/41* (2006.01)
*C07C 57/10* (2006.01)

(52) U.S. Cl. ............ 554/161; 554/224; 554/34; 554/74; 554/75; 554/78; 554/156

(58) Field of Classification Search .......................... None
See application file for complete search history.

(56) References Cited

U.S. PATENT DOCUMENTS 6,022,916 A 2/2000 Enlow

FOREIGN PATENT DOCUMENTS

WO WO 2005108535 * 11/2005
WO WO 2009/032728 * 3/2009

OTHER PUBLICATIONS

Stanley D. Koch, et al.; "Basis of Stability of Amine Salts of Linoleic Acid 1. Generality of the Oxidation Protection and Effect of Physical State", Journal of Food Science, vol. 36, No. 3, 1971, pp. 477-481.
BASF Corporation Brochure: "Dry n-3 18:12 Enrich Your Dietary Supplements with Healthful Omega-3 Fatty Acids", 2005.
Kralovec J. A., et al: "Production and bioavailability of calcium and magnesium salts of omega-3 fatty acids", Journal of Functional Foods, vol. 1, Feb. 2009, pp. 217-221.
European Search Report from corresponding European Application No. 11159605, mailed Apr. 5, 2012.

* cited by examiner

*Primary Examiner* — Yate K Cutliff
(74) *Attorney, Agent, or Firm* — Polster, Lieder, Woodruff & Lucchesi, L.C.

(57) ABSTRACT

A co-salt of a polyunsaturated fatty acid and a non-fatty acid is formed as a precipitate. The co-salt formed is free flowing and does not tend to agglomerate (cake) in storage. The resultant co-salt product will be easy to blend with other products to produce dietary supplements. These novel co-salt products may also tablet very well and may be added to current dietary supplement tablets.

20 Claims, 3 Drawing Sheets

CO-PRECIPITATED SALTS OF FATTY ACIDS

CROSS-REFERENCE TO RELATED APPLICATIONS

This application is a continuation of U.S. application Ser. No. 12/731,981 filed Mar. 25, 2010, now U.S. Pat. No. 8,178,707, and which is incorporated herein by reference.

STATEMENT REGARDING FEDERALLY SPONSORED RESEARCH OR DEVELOPMENT

Not Applicable.

BACKGROUND

The present invention relates to the preparation of co-salts of polyunsaturated fatty acids (PUFA) and another anion such as citrate, phosphate, lactate, fumarate, gluconate, carbonate, bicarbonate, malate, or other anions of common acids and the co-precipitated salts of the fatty acid and the anion. The present invention particularly relates to mixtures of monovalent and divalent metal salts rich in omega-3 and omega-6 fatty acids including eicosapentaenoic acid (EPA), docosahexaenoic acid (DHA), docosapentaenoic acid (DPA), eicosatetraenoic acid (ETA), heneicosatetraenoic acid (HPA), linoleic acid (LA), alpha linolenic acid (ALA) and arachidonic acid (ARA), in general known as omega-3 or -6 fatty acids.

Several salts, such as calcium, magnesium, copper, zinc, iron, manganese, potassium, ammonium, sodium, and several others have long been recognized as beneficial mineral nutrients for humans and certain companion animals and livestock, such as dogs, cats, cattle, horses, goats, pigs, birds, fish and others. Calcium is known to be essential for the maintaining of bones and teeth. It is also responsible for a normal heartbeat and helps regulate blood pressure. The divalent cation magnesium acts as a calcium antagonist at the cell membrane level which is necessary to maintain normal electrical potentials and to coordinate muscle contraction-relaxation responses. Additionally, magnesium has roles in energy metabolism as a required cofactor for enzymes that catalyze fatty acid synthesis, protein synthesis, and glucose metabolism. Copper is utilized as an enzyme for many biochemical reactions within the biological system of birds and mammals. Copper deficiency is known to cause anemia, bone disorders, neonatal ataxia, cardiovascular disorders, and many other maladies due to the inability of certain enzymes functioning properly.

Zinc also is essential for protein synthesis, integrity of cell membranes, maintenance of DNA and RNA, tissue growth and repair, wound healing, taste acuity, prostaglandin production, bone mineralization, proper thyroid function, blood clotting and cognitive functions.

A variety of omega-3 fatty acids have been identified as desirable for producing a diversity of nutritional and physiological benefits in humans and lower animals and accordingly have found value as nutritional supplements for a wide variety of animals. In certain animals, omega-3 fatty acids, for example, have been discovered to promote fertility, promote healthy skin and coat, reduce inflammation, and have other nutritional and physiological properties as well. In humans, it is believed that omega-3 fatty acids such as EPA and DHA support healthy cardiovascular function and are important for visual and neuronal development, support healthy blood levels of cholesterol, triglycerides and very low density lipoproteins, ease the inflammation associated with overuse of joints, and improve carbohydrate metabolism. The FDA allows the following claim to be added to products that contain omega-3:

"Supportive but not conclusive research shows that consumption of EPA and DHA omega-3 fatty acids may reduce the risk of coronary heart disease."

In developing fetuses and children, omega-3 fatty acids have been shown to be necessary for the eyes, brain, and developing central nervous system. In adults, omega-3 fatty acids have been shown to maintain normal cardiovascular function and maintain healthy brain and immune system function.

It has also been shown that supplementing the diet of livestock with omega-3 fatty acids will alter the livestock fatty acid profile, so that, for example, feeding dairy cows and beef cattle a source of these unsaturated fatty acids will yield dairy and beef products for human consumption enriched with the beneficial polyunsaturated fatty acids (PUFA).

BRIEF SUMMARY

Generally salts of PUFA's have poor flow and processing characteristics. We have found that Ca and Mg salts of mixed anions comprised of a portion of omega fatty acids and a portion of at least one co-anion such as citrate and phosphate yield new chemical entities that are easy to handle during manufacture, and thus are easier to centrifuge, wash, and dry. Other salts of mixed cations, such as salts of Cu, Zn, Na, K, Mn Fe, Cu, $NH_4$ should also produce acceptable products. Other co-anions include, lactic acid, fumaric acid, malic acid, gluconic acid, acetic acid, ascorbic acid, aspartic acid, carbonic acid, sulfuric acid, phosphoric acid, formic acid, propionic acid, succinic acid, adipic acid, salicyclic acid, benzoic acid, phthalic acid, maleic acid, malonic acid, pyruvic acid, sorbic acid, caprylic acid, glutaric acid, pimelic acid, glucoheptanoic acid, glycerophosphoric acid, glutamic acid, glutathione, lecithin, phenylalanine, valine, leucine, isoleucine, threonine, methionine, lysine, arginine, histidine as well as others. The polyprotic acids may be present in their respective states of protonation. The co-salt products are free flowing and do not tend to agglomerate (cake) in storage. The co-salt may be crystalline. The resultant co-salt product will be easy to blend with other products to produce dietary supplements. These novel co-salt products may also tablet very well and may be added to current dietary supplement tablets.

Briefly stated, a co-salt of the claimed invention is comprised of at least a PUFA anion and at least one non-fatty acid co-anion. The co-anion is less waxy, less hydrophobic and more structurally rigid than the PUFA anion. The co-salt contains at least one cation which is ionically bonded with the PUFA anion and at least one co-anion.

The co-salt has an infrared spectra in which characteristic modes for the co-salt are off-set from corresponding characteristic modes for an admixture of the fatty acid salt and co-anion salt of the co-salt. Thus, for example, in a calcium phosphate co-salt, in which the co-salt has a calcium fatty acid salt component and a calcium phosphate component, the characteristic P—O stretching mode for the phosphate group in the co-salt is shifted relative to the characteristic P—O stretching mode for the phosphate group for an admixture of calcium fatty acid salt and calcium phosphate. Similarly, the $COO^-$ modes for the co-salt are off-set from the $COO^-$ modes for the calcium fatty acid salt.

The fatty acid anion and the co-anion vary in relative concentrations from about 10% fatty acid anion and 90% co-anion to about 90% fatty acid anion and 10% co-anion; and preferably the co-salt is about 40% to about 80% fatty acid anion and about 60% to about 20% co-anion. The cation is chosen from the group consisting of calcium, magnesium, zinc, iron, manganese, copper, potassium, sodium, ammonium, and combinations thereof.

At least one co-anion is chosen from the group consisting of citric acid, lactic acid, phosphoric acid, fumaric acid, malic acid, gluconic acid, acetic acid, ascorbic acid, aspartic acid, carbonic acid (as carbonate and bicarbonate), sulfuric acid (as both sulfate and bisulfate ions), phosphoric acid (monobasic, dibasic and tribasic), formic acid, propionic acid, succinic acid, adipic acid, salicyclic acid, benzoic acid, phthalic acid, maleic acid, malonic acid, pyruvic acid, sorbic acid, caprylic acid, glutaric acid, pimelic acid, glucoheptanoic acid, glycerophosphoric acid, glutamic acid, glutathione, lecithin, phenylalanine, valine, leucine, isoleucine, threonine, methionine, lysine, arginine, histidine, and the like and combinations thereof.

The fatty acid anion comprises at least one omega-3 or omega-6 fatty acid. The co-salt is least 5% by weight omega-3 or omega-6 fatty acids; and preferably, 15% to 95% omega-3 or omega-6 fatty acids.

The omega-3 fatty acid is chosen from the group consisting of alpha-linolenic acid (C18:3, n-3), eicosatetraenoic acid (C20:4, n-3), moroctic acid (C18:4, n-3), eicosapentaenoic acid (EPA) (C20:5, n-3), heneicosapentaenoic acid (C21:5, n-3), docosapentaenoic acid (C22:5, n-3), and docosahexaenoic acid (DHA) (C22:6, n-3), and combinations thereof. The omega-6 fatty acid is chosen from the group consisting of linoleic acid 18:2 (n-6), eicosatrienoic acid 20:3 (n-6), arachidonic acid 20:4 (n-6), and combinations thereof.

In accordance with one aspect, the fatty acid anion comprises a complex mixture of multiple omega fatty acid anions and other fatty acid anions. This complex mixture of fatty acids can be derived from:
  (a) fish oils, seed oils, or microbial oils, or
  (b) esters of fish oils, seed oils, or microbial oils, or
  (c) triglycerides resulting from the re-esterification of purified esters from fish oils, seed oils, microbial oils.

In accordance with one aspect of the co-salt, the fish oil is 18% by weight EPA and 12% by weight DHA.

In accordance with one aspect of the co-salt, the ratio of the fatty acid anion to the non-fatty acid co-anion ranges from about 50:50 to 70:30, the cation for the salts is calcium or magnesium, the non-fatty acid salt is citrate or phosphate; and the omega-3 fatty acid content comprises about 15-47% of the weight of the co-salt.

The co-salt is produced by forming a salt solution comprised of a soluble fatty acid salt and a soluble non-fatty acid salt; adding a water solution of MX or $MX_2$ to the salt solution to form a reaction solution, where M is a divalent or monovalent cation, or mixtures of divalent and/or monovalent cations, and X is a water soluble anion; and then filtering the co-salt precipitate from the solution. After the precipitate has been filtered, it can be dried. It will be appreciated that the soluble fatty acid salt may, in fact, be a mixture of fatty acid salts.

The MX or $MX_2$ is added to the salt solution in an equimolar amount of the cation to the combined molar amount of the anions of salt solution.

In accordance with one aspect of the method, the salt solution is formed by combining a solution of a soluble fatty acid salt and a solution of a soluble non-fatty acid salt. In a preferred method, the soluble non-fatty acid salt solution is added to the soluble fatty acid salt in solution. In accordance with another aspect of the method, the salt solution is formed by producing an anion solution comprised of a fatty acid anion and a non-fatty acid anion; and adding a cation to the anion solution which will combine with the fatty acid and non-fatty acid to form soluble fatty acid salts and soluble non-fatty acid salts. The salt solution comprises sodium, potassium or ammonium fatty acid and non-fatty acid salts. Hence, in the second method of forming the salt solution, the cation is sodium, potassium or ammonium.

In the cation solution which is added to the salt solution, M is chosen from the group consisting of Ca, Mg, Cu, Zn, Fe, Mn, K, Na, $NH_4$ and combinations thereof; and X is chosen from the group consisting of $Cl^-$, $NO_3^-$, $SO_4^{-2}$, acetate, formate, carbonate, bicarbonate, and the like and combinations thereof.

BRIEF DESCRIPTION OF THE SEVERAL VIEWS OF THE DRAWINGS

Corresponding reference numerals will be used throughout the several figures of the drawings.

DETAILED DESCRIPTION

The following detailed description illustrates the invention by way of example and not by way of claimed limitation. This description will clearly enable one skilled in the art to make and use the claimed invention, and describes several embodiments, adaptations, variations, alternatives and uses of the claimed invention, including what we presently believe is the best mode of carrying out the claimed invention. Additionally, it is to be understood that the claimed invention is not limited in its application to the details of construction and the arrangements of components set forth in the following description or illustrated in the drawings. The claimed invention is capable of other embodiments and of being practiced or being carried out in various ways. Also, it is to be understood that the phraseology and terminology used herein is for the purpose of description and should not be regarded as limiting.

It has been found that co-precipitated anion co-salts can be produced that yield easy to handle free flowing compounds. These co-precipitated salts can be comprised of a cation such as Ca or Mg and a mixture of at least one fatty acid anion and at least one non-fatty acid co-anion. Other cations, such as Fe, Mn, K, Cu, Zn, and Na or other divalent or monovalent metal ions may also be acceptable. The fatty acid anion for the co-salt can be a mixture of omega fatty acids obtained from commercial fish oils or seed oils or their esters or re-esterified products by saponification as well as DHA/EPA enhanced fatty acids or esters that are commercially available. These fatty acids can be obtained from microbial products (algae) as well. The mixture of omega fatty acids can include alpha-linolenic acid, moroctic acid, eicosatetraenoic acid, eicosapentaenoic acid (EPA), heneicosapentaenoic acid, docosapentaenoic acid, docosahexaenoic acid (DHA), arachidonic acid (ARA), and alpha linoleic acid. The co-anion of the co-salt can be selected from any of a large number of commercial acids such as citric, lactic, phosphoric, fumaric, malic, gluconic, carbonic, sulfuric, and the like. Acetic acid, ascorbic acid and aspartic acid or any other organic or inorganic acid that will form salts with the above-noted cations can be used for the second anion. Additionally, formic acid, propionic acid, succinic acid, adipic acid, salicyclic acid, benzoic acid, phthalic acid, maleic acid, malonic acid, pyruvic acid, sorbic acid, caprylic acid, glutaric acid, pimelic acid, glucoheptanoic acid, glycerophosphoric acid, glutamic acid, glutathione, lecithin, phenylalanine, valine, leucine, isoleucine, threonine, methionine, lysine, arginine, histidine could be used as well. It will be understood that the polyprotic acids may be present in their respective states of protonation. The final product (i.e., the co-salt) is granular and free flowing, and can be utilized in products that are meant to be fortified with mineral salts and omega fatty acids. The product can be crystalline (or can exhibit some degree of crystallinity).

In practice, a complex and variable mixture of omega fatty acids is expected to be used in producing the mixture. Thus, for example, a final product of a 50:50 co-precipitated calcium co-salt with citric acid and omega-3 acid anions will contain various mixtures of the individual fatty acids obtained from the original oil. For example, menhaden oil, a common fish oil, can provide the acids found in Table 1, below.

TABLE 1

MENHADEN OIL - TYPICAL FREE FATTY ACID PROFILE

| Fatty Acid (Chain Length:Number of Double Bonds) | Weight % in Menhaden Oil |
|---|---|
| Myristic Acid 14:0 | 10.86 |
| 15:0 | 0.67 |
| Palmitic Acid 16:0 | 18.20 |
| Palmitoleic 16:1 (n – 7) | 13.79 |
| 16:2 (n – 4) | 2.35 |
| 16:4 (n – 1) | 2.34 |
| 17:0 | 0.64 |
| Stearic Acid 18:0 | 2.89 |
| Oleic Acid 18:1 (n – 9) | 9.60 |
| 18:1 n – 7 | 3.57 |
| 18:2 n – 6 | 1.60 |
| Linoleic Acid 18:2 (n – 6) | 1.60 |
| alpha-Linolenic Acid 18:3 (n – 3) | 1.23 |
| Stearidonic Acid 18:4 (n – 3) | 3.63 |
| 20:1 (n – 9) | 1.53 |
| Eicosatrienoic Acid 20:3 (n – 6) | 0.19 |
| Arachidonic Acid 20:4 (n – 6) | 0.89 |
| 20:4 (n – 3) | 1.43 |
| Eicosapentaenoic Acid 20:5 (n – 3) (EPA) | 13.87 |
| Docosapentaenoic Acid 22:5 (n – 3) | 1.86 |
| Docosahexaenoic Acid 22:6 (n – 3) (DHA) | 7.10 |

Reference: Yang, L. Y.; Kuksis, A.; Myher, J. J., Journal of Lipid Research, Vol. 31, 1990, p. 37

Each of these fatty acids will be contained in the final product as the salt of the particular fatty acid in the same mole ratio found in the original oil. The mixture of fatty acids has a fixed average molecular weight that is determined by titration. The total variety of acid anions obtained from each oil will be called, for ease, "omega-ate" when these anions are incorporated in a salt. For example, in a 50:50 co-salt of calcium citrate with the fatty acids of the above fish oil, the initial amount of DHA would be 50% of 7.1% or 3.55% based on the chart above factored down to account for the calcium and water in the final product. The co-anion would be citrate and the mixture of the above fatty acids from the fish oil would be "omega-ate".

In naming these co-precipitated co-salts, the nominal ratio, (say for a 70:30 co-salt) describes the relative weights of the two salts present in the product. The first value describes the weight percent of the fatty acid salt. The second value describes the weight percent of the non-fatty acid salt. For example, a "70:30 calcium citrate co-salt" would describe a co-salt comprised of 70% by weight calcium omega-ate salt and 30% by weight calcium citrate.

The Tables 3-5 below show results of calculations of theoretical total percent of calcium (or magnesium) of the co-precipitated salt using fish oil having different amounts of omega fatty acids and for varying ratios of the free fatty acid to the secondary non-free fatty acid anion. The calculations are based on a single admixture of a calcium fatty acid salt and calcium citrate-tetrahydrate. Tables 3-5 are intended to depict the range of possible product concentrations of both the mineral nutrient, either calcium or magnesium, and the omega-3 content from varying the omega-3 content of the starting fish oil or from varying the ratio of the two anions. Table 2 below is a two-axis table showing, along the vertical axis, the various co-anions that can be used, and along the horizontal axis, the various cations that can be used in the production of the co-salt. It will be understood that any co-salt produced will also include a fatty acid component as well.

TABLE 2

Co-anion - Cation table

| | Ca | Mg | Cu | Zn | Fe | Mn | K | Na | NH₄ |
|---|---|---|---|---|---|---|---|---|---|
| acetic acid | | | | | | | | | |
| adipic acid | | | | | | | | | |
| arginine | | | | | | | | | |
| ascorbic acid | | | | | | | | | |
| aspartic acid | | | | | | | | | |
| benzoic acid | | | | | | | | | |
| caprylic acid | | | | | | | | | |
| carbonic acid | | | | | | | | | |
| citric acid | | | | | | | | | |
| formic acid | | | | | | | | | |
| fumaric acid | | | | | | | | | |
| glucoheptanoic acid | | | | | | | | | |
| gluconic acid | | | | | | | | | |
| glutamic acid | | | | | | | | | |
| glutaric acid | | | | | | | | | |
| glutathione | | | | | | | | | |
| glycerophosphoric acid | | | | | | | | | |
| histidine | | | | | | | | | |
| isoleucine | | | | | | | | | |
| lactic acid | | | | | | | | | |
| lecithin | | | | | | | | | |
| leucine | | | | | | | | | |
| lysine | | | | | | | | | |
| maleic acid | | | | | | | | | |
| malic acid | | | | | | | | | |
| malonic acid | | | | | | | | | |
| methionine | | | | | | | | | |
| phenylalanine | | | | | | | | | |
| phosphoric acid | | | | | | | | | |
| phthalic acid | | | | | | | | | |
| pimelic acid | | | | | | | | | |
| propionic acid | | | | | | | | | |
| pyruvic acid | | | | | | | | | |
| salicyclic acid | | | | | | | | | |
| sorbic acid | | | | | | | | | |
| succinic acid | | | | | | | | | |
| sulfuric acid | | | | | | | | | |
| threonine | | | | | | | | | |
| valine | | | | | | | | | |

In preparing the co-salt, any of the cations can be paired with any of the co-anions. Thus, the co-salt can be made using calcium as the cation and citric acid as the co-anion. Alternatively, sodium (Na) can be used as the cation with ascorbic acid as the co-anion. Further, although the examples below disclose compounds which use only a single co-anion and only a single cation, the co-salt can be formed using two or more cations and/or using two or more co-anions. Hence, for example a co-salt could be prepared using, as anions, an omega-ate, citric acid and malic acid. Similarly, a co-salt could be prepared using calcium and magnesium as cations. If a single cation (e.g., calcium) is used with the two co-anions (e.g., citric acid and malic acid), a calcium-omega-ate/malate/citrate co-salt would be produced. If only one secondary anion (e.g., citric acid) and two cations (e.g., calcium and magnesium) were used, a calcium/magnesium-omega-ate/citrate co-salt would be produced. Finally, if two secondary anions (e.g., citric acid and malic acid) and two cations (e.g., calcium and magnesium) were used, the resulting co-salt would be a calcium/magnesium-omega-ate/citrate/malate co-salt would be produced. The co-salt could also be prepared using more than two cations and/or more than two secondary anions.

The concentration of the omega-3 of the co-salt is fixed by the origin of the free fatty acid (FFA). For the "70:30 calcium citrate co-salt" example of Table 3, below, if the original free fatty acid contained 30% EPA+DHA, then the final product would contain 21% by weight calcium salts of EPA+DHA, and would contain 10.9% by weight calcium. As can be appreciated, the percent by weight calcium in the co-salt includes the calcium in both the fatty acid salt and the non-fatty acid salt.

The ratio of the FFA anions to the non-fatty acid anion can range from about 90% FFA by weight (i.e., about a 90:10 ratio) to about 90% non-fatty acid by weight (i.e., about a 10:90 ratio). Thus, for example, in a citrate co-salt, a co-salt can be produced that contains about 90% fatty acid and about 10% of the citrate (about 90:10) while a product at the opposite end of the range can contain about 10% fatty acid and about 90% citrate (about 10:90). Table 3 summarizes an example of the range of products made from a 35% omega-3 fish oil and citrate anions with calcium as the metal ion.

TABLE 3

% Omega-3 Salt and % Calcium Contents for Various Co-Salt Compositions

| Wt % Ca-FFA | Wt % Ca-ω-3 | | | wt % | |
|---|---|---|---|---|---|
| | as EPA | as DHA | Total wt % Ca-ω-3* (EPA + DHA) | Calcium Citrate | Total wt % Calcium |
| 10 | 1.8 | 1.2 | 3.0 | 90 | 19.6 |
| 30 | 5.4 | 3.6 | 9.0 | 70 | 16.7 |
| 45 | 8.1 | 5.4 | 13.5 | 55 | 14.5 |
| 50 | 9.0 | 6.0 | 15.0 | 50 | 13.8 |
| 60 | 10.8 | 7.2 | 18.0 | 40 | 12.3 |
| 65 | 11.7 | 7.8 | 19.5 | 35 | 11.6 |
| 70 | 12.6 | 8.4 | 21.0 | 30 | 10.9 |
| 90 | 16.2 | 10.8 | 27.0 | 10 | 8.0 |

*This column contains the % by weight calcium EPA + DHA. Actual EPA + DHA content, as the free acid, is calculated based on the starting average free fatty acid molecular weight. For example, a 1,000-mg tablet of a "70:30 calcium citrate co-salt" would contain 196-mg EPA + DHA, and 109-mg calcium.

Table 4 shows the same 35% omega-3 fish oil product using magnesium phosphate as the co-salt.

TABLE 4

% Omega-3 Salt and % Magnesium Contents for Various Co-Salt Compositions

| wt % Mg-FFA | wt % Mg-Ω-3 | | | wt % Mg Phosphate | total wt % Mg |
|---|---|---|---|---|---|
| | as EPA | as DHA | Total % Mg-Ω3 (EPA + DHA) | | |
| 30 | 5.4 | 3.6 | 9.0 | 70 | 15.7 |
| 45 | 8.1 | 5.4 | 13.5 | 55 | 13.2 |
| 50 | 9.0 | 6.0 | 15.0 | 50 | 12.4 |
| 60 | 10.8 | 7.2 | 18.0 | 40 | 10.7 |
| 65 | 11.7 | 7.8 | 19.5 | 35 | 9.9 |
| 90 | 16.2 | 10.8 | 27.0 | 10 | 5.8 |

If the omega-3 percentage in the starting oil is increased to 65%, the results in Table 5 are produced for an array of calcium phosphate co-salts:

TABLE 5

% Omega-3 Salt and % Calcium Contents for Various Co-Salt Compositions

| wt % Ca-FFA | wt % Ca-Ω-3 | | | wt % Ca Phosphate | total wt % Ca |
|---|---|---|---|---|---|
| | as EPA | as DHA | Total % Ca-Ω3 (EPA + DHA) | | |
| 30 | 11.7 | 7.8 | 19.5 | 70 | 29.8 |
| 45 | 17.6 | 11.7 | 29.3 | 55 | 24.8 |
| 50 | 19.5 | 13.0 | 32.5 | 50 | 23.1 |
| 60 | 23.4 | 15.6 | 39.0 | 40 | 19.7 |
| 65 | 25.4 | 16.9 | 42.3 | 35 | 18.1 |
| 90 | 35.1 | 23.4 | 58.5 | 10 | 9.7 |

It is clear that there is a wide variety of products that will contain different amounts of the cation and the omega-ate anions.

Figure 1:
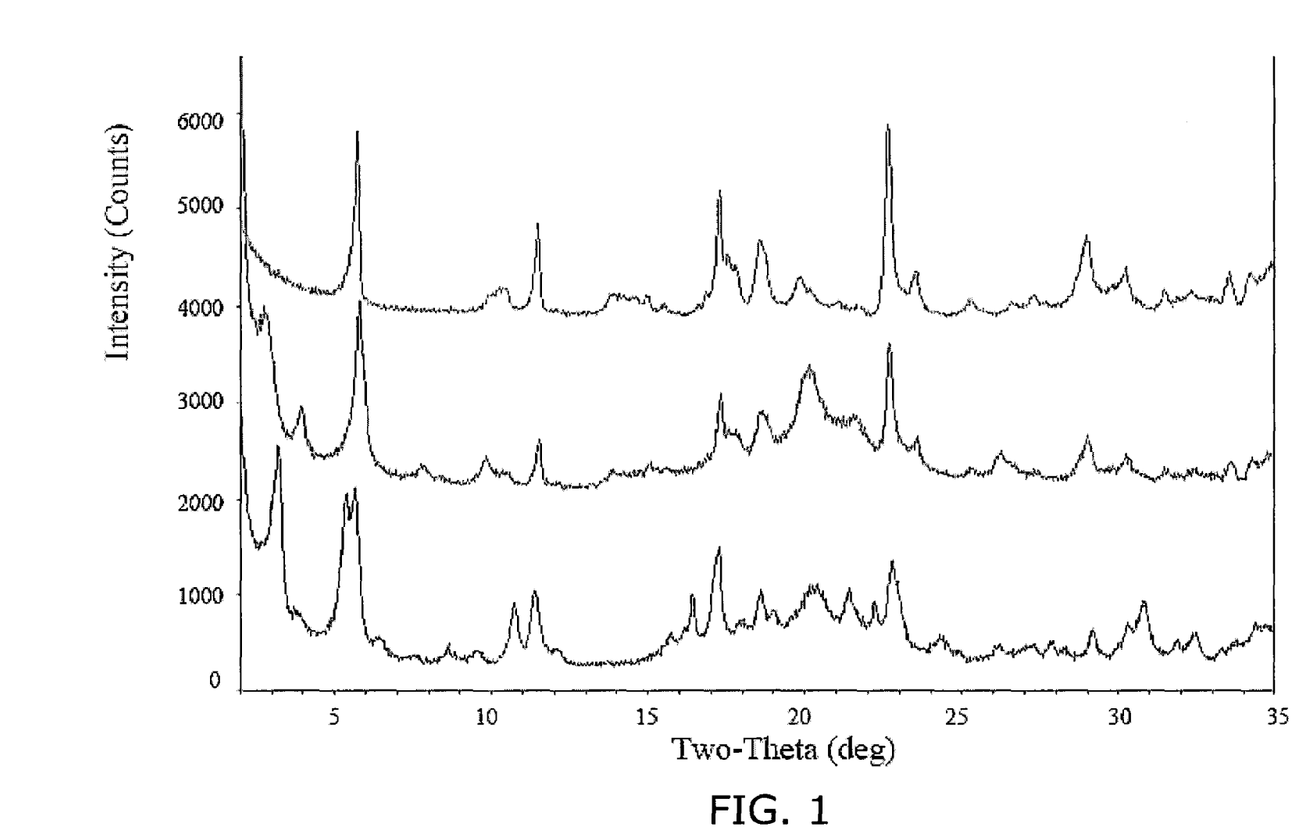
FIG. 1 shows X-ray Diffraction Patterns of (1) a 50:50 Calcium Citrate Calcium/Fatty Acid Co-Salt (bottom line) prepared in accordance with the claimed invention; (2) Calcium Citrate (top line) and (3) a 50:50 admixture of Calcium Fatty Acid Salt and Calcium Citrate salt (middle line)

Evidence of New Compound:

FIG. 1 shows X-ray Diffraction Patterns of (1) a 50:50 Calcium Citrate Calcium/Fatty Acid Co-Salt (bottom line) prepared in accordance with the method described below; (2) Calcium Citrate (top line) and (3) a 50:50 admixture of Calcium Fatty Acid Salt and Calcium Citrate salt (middle line). An admixture is defined simply as a mixture in which the mixture components (calcium fatty acid salt and calcium citrate salt in this example) are dry-blended together. As seen from FIG. 1, the X-ray diffraction patterns indicate that there is some crystallinity in the co-salt. The X-ray diffraction of FIG. 1 makes clear that the 50:50 precipitated co-salt product is different from a 50:50 dry blend or admix of the calcium citrate and calcium fatty acid salt.

Figure 3:
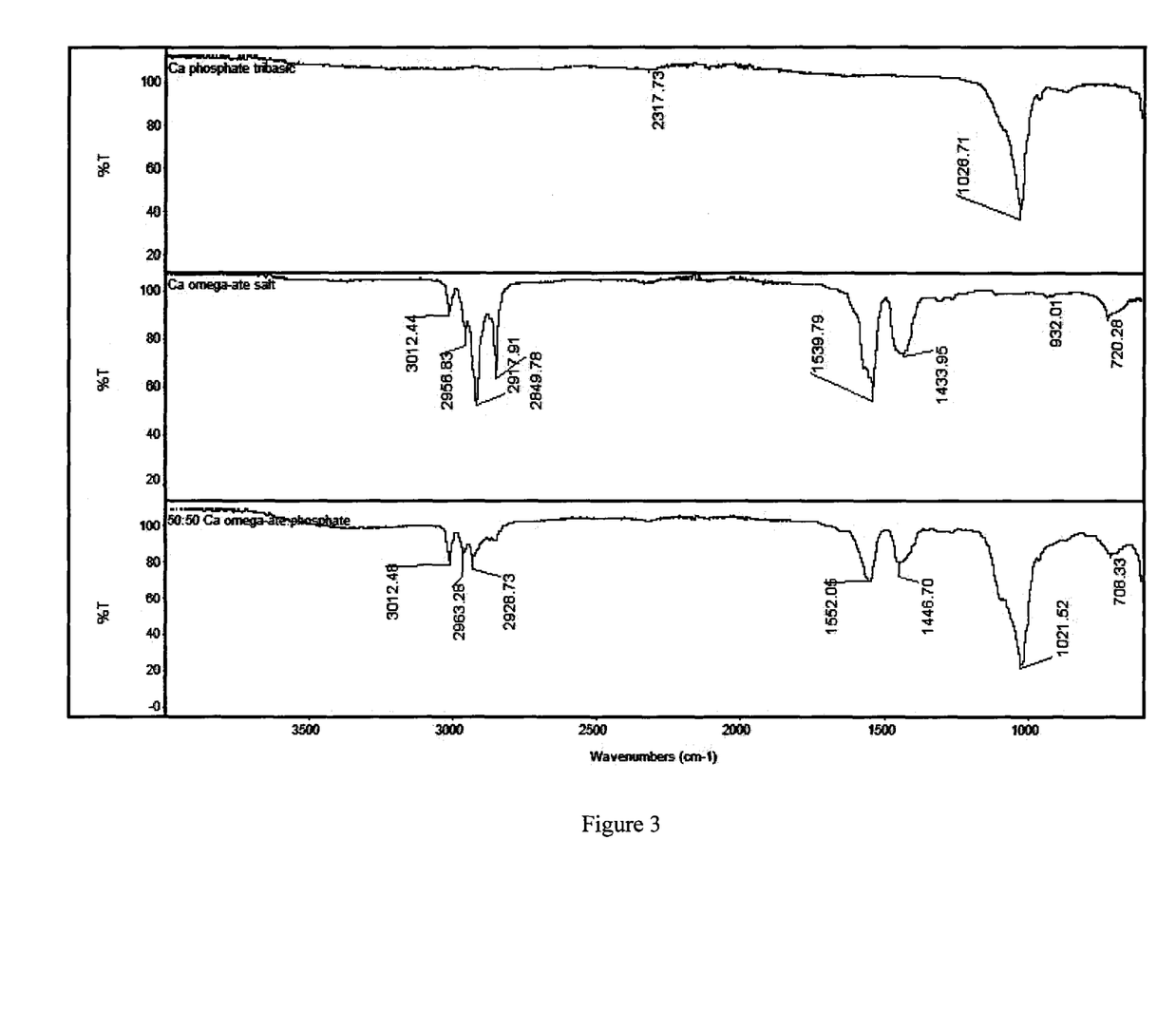
FIG. 3 is an infrared spectra of calcium phosphate tribasic, a calcium salt derived from omega-3 fish oil, and a co-precipitated calcium co-salt containing phosphate and the omega-3 anion.

FIG. 3 shows the infrared spectra of calcium phosphate (top line), a calcium salt derived from fish oil (middle line), and a co-precipitated calcium salt containing phosphate ion and an omega-ate anion (bottom line). The strong band at 1026 $cm^{-1}$ in the spectrum of calcium phosphate is characteristic of a P—O stretching mode for an ionic phosphate group (tetrahedral symmetry). The shift to lower wave numbers (5 $cm^{-1}$) observed for the P—O stretching mode of the phosphate ion in the spectrum of the co-precipitated salt demonstrates that a novel calcium omega-ate phosphate co-salt has formed. The bands of interest in the spectrum of the Ca omega-ate co-salt are the asymmetric and symmetric $COO^-$ stretching modes centered at 1540 $cm^{-1}$ and 1434 $cm^{-1}$, respectively, in the middle line. The shift to higher wave numbers in the spectrum of the co-precipitated salt also indicate a novel calcium omega-ate phosphate co-salt has been formed as opposed to a simple mixture of the two salts.

Figure 2:
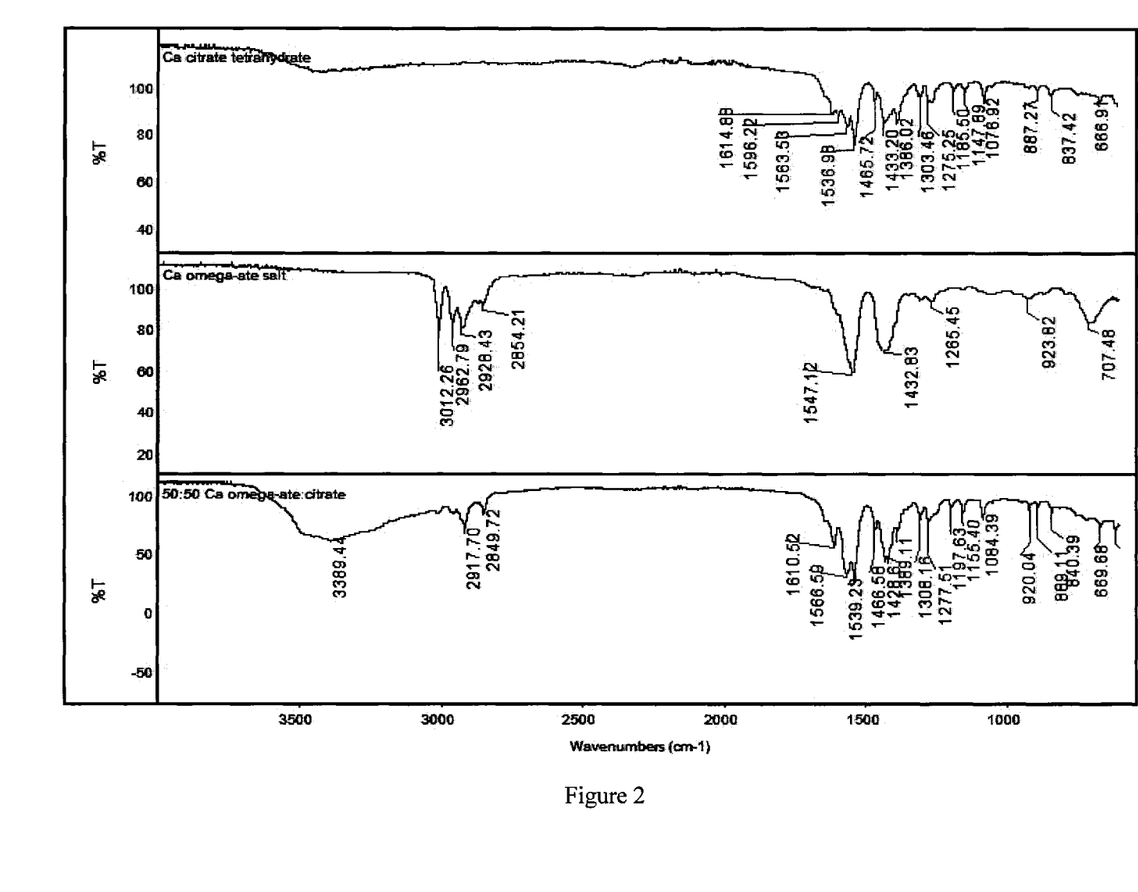
FIG. 2 is an infrared spectra of calcium citrate tetrahydrate, a calcium salt derived from an omega-3 fish oil, and a co-precipitated calcium co-salt containing citrate anion and an omega-3 anion.

FIG. 2 shows the infrared spectra of calcium citrate (top line), a calcium salt derived from omega-ate fish oil fatty acids (middle line), and a co-precipitated calcium co-salt containing citrate and omega-ate anions (bottom line), hereafter called calcium citrate 50:50 co-salt. The bands of interest are the asymmetric and symmetric COO$^-$ stretching vibrations centered at approximately 1550 cm$^{-1}$ and 1430 cm$^{-1}$, respectively, in the middle line, and the wagging and scissoring modes in the region of 600 to 1310 cm$^{-1}$, which are more well defined in the spectra of calcium citrate (top line) and the co-precipitated co-salt (bottom line). The change in splitting patterns and shifts in wave number of the COO$^-$ stretching vibrations observed in the spectrum of the co-precipitated salt relative to the same modes in the spectra of calcium citrate or calcium omega-ate demonstrate the formation of a novel compound, as opposed to a simple mixture of the two salts. For example, the symmetric COO$^-$ stretching vibrations mode is characterized by a strong doublet observed at 1433 cm$^{-1}$ and 1386 cm$^{-1}$ in the spectrum of calcium citrate, whereas the symmetric COO$^-$ stretching vibrations mode is characterized by a unique singlet at 1429 cm$^{-1}$ in the spectrum of the co-precipitated co-salt. Furthermore, the wagging and scissoring modes observed in the region of 600 cm$^{-1}$ to 1310 cm$^{-1}$ remain well defined in the spectrum of the co-precipitated co-salt but are shifted to higher wave numbers, further demonstrate the formation of a novel species.

GENERAL PREPARATION AND WORKING EXAMPLES

The co-precipitated co-salt is produced by preparing a solution of a soluble fatty acid (omega-ate) salt and a co-anion salt. The salt solution is prepared at ambient or room temperature (i.e., approximately 25-32° C.) The salt of the anions can be a sodium salt. Potassium or ammonium are expected to work as well. The soluble salt solution can be prepared two ways. In a first method, a co-anion salt solution is added to a fatty acid salt solution. In a second method, the anions (i.e., the omega-ate ions and the co-anion) are combined and, for example, a sodium solution (i.e., an NaOH solution) is added to the anion solution to form the fatty acid and co-anion salts. In the first noted method, the sodium salt solution of the free fatty acid can be derived from saponifying fish oils, the ethyl or methyl esters of fish oil fatty acids or from transesterification of those oils. The same technique can be applied to seed oils, microbial oils and re-esterified omega-3 acid products.

Possible choices for co-anions include citric acid, lactic acid, phosphoric acid, fumaric acid, malic acid, gluconic acid, acetic acid, ascorbic acid, aspartic acid, carbonic acid, or sulfuric acid, formic acid, propionic acid, succinic acid, adipic acid, salicyclic acid, benzoic acid, phthalic acid, maleic acid, malonic acid, pyruvic acid, sorbic acid, caprylic acid, glutaric acid, pimelic acid, glucoheptanoic acid, glycerophosphoric acid, glutamic acid, glutathione, lecithin, phenylalanine, valine, leucine, isoleucine, threonine, methionine, lysine, arginine, histidine and the like and combinations thereof. As noted above, the polyprotic acids may be present in their respective states of protonation. This soluble salt solution is viscous.

After the soluble salt solution has been prepared, an exchange reaction is performed in which, with vigorous stirring, a water solution of MX or MX$_2$ is added (where M can be Ca, Mg, Cu, Zn, Fe, Mn, or other divalent cations and X is a water soluble anion such as Cl$^-$, NO$_3^-$, SO$_4^{-2}$, acetate, formate, and the like). The co-salt immediately begins precipitating with the addition of the metal salt solution (different metal salts have slightly different solubilities). After addition of at least a stoichiometrically equivalent amount of cation to the combined molar amount of the two anions, the solution is digested for an hour. It is then filtered, washed with water, and dried. The final product is a solid free flowing material.

Without the second anion, it has been demonstrated that many of the metal salts of the pure oils are waxy and do not filter or dry well. They also do not blend well with other products. The reaction of the second anion contributes to improved handling properties of these products.

EXAMPLES

Table 6 below presents experimental data showing various co-salts that have been produced employing the general co-precipitation procedure described above. Specific and detailed "working examples", described later, elaborate on the concept. In addition, Table 6 provides the theoretical weight percents of the omega-3 fatty acid (i.e., combined EPA and DHA) and the theoretical weight percent of the cation (i.e., calcium or magnesium). As described above, the theoretical weight percents are calculated assuming an admixture of the omega-ate salt with calcium citrate tetrahydrate, calcium phosphate, and magnesium phosphate.

TABLE 6

Summary of Analysis of Composition of Co-Salts Prepared by Coprecipitation
(All %-values are weight %)

| Co-Salt Description | | % DHA | % EPA | Total % [EPA + DHA] | wt % cation | % Moisture Wt Loss by TGA | Theoretical Wt % EPA + DHA | Theoretical wt % Cation |
|---|---|---|---|---|---|---|---|---|
| Calcium Citrate Co-Salts | | | | | | | | |
| % Ca-FFA | % Ca-Citrate | | | | | | | |
| 10 | 90 | 1.31 | 1.66 | 3.0 | 20.4 | | 3.0 | 19.6 |
| 10 | 90 | 0 | 0.1 | 0.1 | 18.0 | | 3.0 | 19.6 |
| 52 | 48 | 7.69 | 8.80 | 16.5 | 12.0 | 7.4 | 18.7 | 13.5 |
| 50 | 50 | 4.98 | 6.54 | 11.5 | 12.6 | 3.0 | | 13.8 |
| 50 | 50 | 4.24 | 6.04 | 10.3 | | | | |
| 50 | 50 | 2.06 | 3.39 | 5.5 | 12.0 | 3.7 | 15.0 | 13.8 |
| 70 | 30 | 9.66 | 12.05 | 21.7 | 10.6 | 2.3 | 21.0 | 10.9 |

TABLE 6-continued

Summary of Analysis of Composition of Co-Salts Prepared by Coprecipitation
(All %-values are weight %)

| Co-Salt Description | | % DHA | % EPA | Total % [EPA + DHA] | wt % cation | % Moisture Wt Loss by TGA | Theoretical Wt % EPA + DHA | Theoretical wt % Cation |
|---|---|---|---|---|---|---|---|---|
| 70 | | 30 | 3.38 | 4.95 | 8.3 | 10.1 | 4.0 | 21.0 | 10.9 |
| 90 | | 10 | 10.96 | 13.93 | 24.9 | 7.0 | 2.0 | 27.0 | 8.0 |

Calcium Phosphate Co-Salts

| % Ca-FFA | % Calcium Phosphate | | | | | | | |
|---|---|---|---|---|---|---|---|---|
| 50 | 50 | 6.67 | 8.26 | 14.9 | 20.8 | 2.0 | 15.0 | 23.2 |
| 70 | 30 | 9.06 | 11.21 | 20.3 | 14.7 | 6.0 | 21.0 | 16.5 |
| 30 | 70 | 3.82 | 4.78 | 8.6 | 26.6 | 2.5 | 9.0 | 29.9 |
| 50 (high ω-3-FFA) | 50 | 10.40 | 35.96 | 46.3 | 20.8 | 2.2 | 47.0 | 23.0 |

Magnesium Phosphate Co-Salts

| % Mg-FFA | % Mg-Phosphate | | | | | | | |
|---|---|---|---|---|---|---|---|---|
| 50 | 50 | 6.87 | 8.38 | 15.3 | 9.7 | 5.7 | 15.0 | 12.3 |
| 50 | 50 | 6.31 | 7.94 | 14.3 | 10.7 | | 15.0 | 12.3 |
| | | 6.19 | 7.70 | 13.9 | 11.0 | | 15.0 | 12.3 |

The fact that the experimental data differed from the theoretical calculations, as shown in Table 6 above, is further evidence that the co-salt is a novel compound and not simply an admixture of two salts.

Working Example A

Preparation of 50:50 Calcium Omega-3 Salt: Calcium Citrate Tetrahydrate Co-Salt
1. Preparation of Free Fatty Acid Sodium Salt Solution: Assemble a round bottom 2-Liter three-necked flask equipped with a motor-driven Teflon paddle stirrer, a nitrogen purge inlet, a heating mantle, and a 130-mL capacity addition funnel with pressure-equalizing sidearm. Purge thoroughly with nitrogen. Then add 320-mL's degassed deionized water. Continue a slow nitrogen purge throughout the remaining steps.
2. Next, add 46.9 grams of a "free fatty acid" mixture derived from menhaden oil by saponification and having an average equivalent weight of 288 grams/mole.
3. Adjust the temperature of the stirring mixture to 30-32° C. Then add dropwise a solution of 13.0 grams 50% sodium hydroxide dissolved in 100-mL's of degassed deionized water.
4. Preparation of Trisodium Citrate Solution: In a separate 400 mL glass beaker equipped with a magnetic stirbar, and using a stirrer/hot-plate, make a solution by mixing 150-mL's deionized water, 33.7 grams citric acid, and 42.0 grams 50% sodium hydroxide. Use a cooling water bath to cool the solution to 30-32° C.
5. Over a 10-minute period and with rapid stirring, add all of the "Trisodium Citrate solution" to the "Free Fatty Acid Sodium Salt solution". As the addition proceeds, add 200 mL's more degassed deionized water to the stirring mixture.
6. When the addition of the "Trisodium Citrate solution" to the "Free Fatty Acid Sodium Salt solution" is complete, continue rapid stirring of the somewhat viscous solution.
7. Next, begin the dropwise addition of 163 mL's of a 21.5% aqueous solution of calcium chloride. The addition rate is such that about one hour is required for complete addition of the 163-mL's of calcium chloride solution. Precipitation occurs throughout the addition. The final resulting reaction mixture is a thick slurry of white solids.
8. Stir for an additional one hour.
9. Collect the product by vacuum filtering the slurry on a 12.5-cm Buchner Funnel, using a Fisherbrand number 6, glass fiber filter medium. Wash the product with 200-mL's degassed deionized water.
10. Dry the wet product in a vacuum oven to constant weight. The theoretical weight of dry product is 100-grams. Actual obtained dry weight is 98.5-grams.
Product Analysis:
50:50 Calcium Omega-3 Salt: Calcium Citrate Co-Salt
% Calcium=12.6%
% EPA+DHA, by GC Analysis, as fatty acid methyl esters (FAMES)=11.5%
Theoretical Expected % [EPA+DHA]=15.0%
Thermogravimetric Analysis of % Weight Loss on Heating to 120° C.=3.0%
The product is a solid free flowing material.

Working Example B

Preparation of 50:50 Calcium High-Omega-3 Salt: Calcium Phosphate Co-Salt
1. Preparation of Free Fatty Acid Sodium Salt Solution: Assemble a round bottom 2-Liter three-necked flask equipped with a motor-driven Teflon paddle stirrer, a nitrogen purge inlet, a heating mantle, and a 130 mL capacity addition funnel with pressure-equalizing sidearm. Purge thoroughly with nitrogen. Then add 320 mL's degassed deionized water. Continue a slow nitrogen purge throughout the remaining steps.
2. Next, add 47.1 grams of a "free fatty acid" mixture derived by saponification from a highly refined re-esterified fish oil. The free fatty acid has an average equivalent weight of 313 grams/mole. The gas chromatographic assay of the starting re-esterified oil, by fatty acid methyl ester (FAME) analysis was 94% (EPA+DHA).
3. Adjust the temperature of the stirring mixture to 29-31° C. Then add dropwise a solution of 11.5 grams 50% sodium hydroxide dissolved in 100-mL's of degassed deionized water. Adjust the temperature of the solution to 30° C.
4. Preparation of Trisodium Phosphate Solution: In a separate 600-mL glass beaker equipped with a magnetic stirbar, and using a stirrer/hot-plate, make a solution by adding 420-mL's deionized water, followed by 34.6 grams 85% Phosphoric Acid. To the diluted Phosphoric Acid solution, add dropwise 72.5 grams 50% Sodium Hydroxide (0.906 mole). Use a cooling water bath to cool the solution to 30-32° C.
5. Over a 10-minute period and with rapid stirring, add all of the "Trisodium Phosphate solution" to the "Free Fatty Acid Sodium Salt solution". As the addition proceeds, add 300-mL's more degassed deionized water to the stirring mixture.
6. When the addition of the "Trisodium Phosphate solution" to the "Free Fatty Acid Sodium Salt solution" is complete, continue rapid stirring of the somewhat viscous solution. Adjust the temperature to 26° C.
7. Next, begin the dropwise addition of 260-mL's of a 21.5% aqueous solution of calcium chloride. The addition rate is such that about one hour is required for complete addition of the 260-mL's of calcium chloride solution. Precipitation of very small, white solids occurs throughout the addition. The final resulting reaction mixture is a thick slurry of white solids.
8. Stir for an additional one hour.
9. Collect the product by vacuum filtering the slurry on a 12.5-cm Buchner Funnel, using a Fisherbrand number 6, glass fiber filter medium. Wash the product with 300-mL's degassed deionized water.
10. Dry the wet product in a vacuum oven to constant weight. The theoretical weight of dry product is 100-grams. Actual obtained dry weight is 102-grams.
Product Analysis:
50:50 Calcium High-Omega-3 Salt: Calcium Phosphate Co-Salt:
% Calcium=20.8%
% EPA+DHA, by GC Analysis, as fatty acid methyl esters (FAMES)=46.3%
Theoretical Expected % [EPA+DHA]=47.0%
Thermogravimetric Analysis of % Weight Loss on Heating to 120° C.=2.2%
The product is a solid free flowing material.

Working Example C

Preparation of 50:50 Magnesium Omega-3 Salt: Magnesium Phosphate Co-Salt
1. Preparation of Free Fatty Acid Sodium Salt Solution: Assemble a round bottom 2-Liter three-necked flask equipped with a motor-driven Teflon paddle stirrer, a nitrogen purge inlet, a heating mantle, and a 130-mL capacity addition funnel with pressure-equalizing sidearm. Purge thoroughly with nitrogen. Then add 320-mL's degassed deionized water. Continue a slow nitrogen purge throughout the remaining steps.
2. Next, add 46.9 grams of a "free fatty acid" mixture derived from menhaden oil by saponification and having an average equivalent weight of 288 grams/mole.
3. Adjust the temperature of the stirring mixture to 30-32° C. Then add dropwise a solution of 13.0 grams 50% sodium hydroxide dissolved in 100-mL's of degassed deionized water.
4. Preparation of Trisodium Phosphate Solution: In a separate 600-mL glass beaker equipped with a magnetic stirbar, and using a stirrer/hot-plate, make a solution by adding 420-mL's deionized water, followed by 32.6 grams 85% Phosphoric Acid. To the diluted Phosphoric Acid Solution, add dropwise 67.9 grams 50% Sodium Hydroxide. Use a cooling water bath to cool the solution to 30-32° C.
5. Over a 10-minute period and with rapid stirring, add all of the "Trisodium Phosphate solution" to the "Free Fatty Acid Sodium Salt solution". As the addition proceeds, add 200-mL's more degassed deionized water to the stirring mixture.
6. When the addition of the "Trisodium Phosphate solution" to the "Free Fatty Acid Sodium Salt solution" is complete, continue rapid stirring of the somewhat viscous solution. Adjust the temperature to 26° C.
7. Prepare an aqueous solution of magnesium chloride at a concentration of 16% by weight, on an anhydrous $MgCl_2$ basis.
8. Next, begin the dropwise addition of 318-g of the 16% magnesium chloride solution to the stirring mixture of trisodium phosphate and free fatty acid sodium salts. The addition rate for the magnesium chloride solution is such that about one hour is required for complete addition of the 318-g of solution. Precipitation of very small, white solids occurs throughout the addition.
9. Once the addition of the magnesium chloride solution is complete, stir the slurry for 1.5 hours at 25-27° C. The final resulting reaction mixture is a thick slurry of white solids.
10. Collect the product in two separate loads on a lab-scale "IEC Clinical Centrifuge" having a stainless steel basket with a diameter of 5-inches, and using a polypropylene cloth as the filter medium. Each load is washed with 150-mL's deionized water.
11. Dry the wet product in a vacuum oven to constant weight. The theoretical weight of dry product is 100-grams. Actual obtained dry weight is 75-grams, since a portion of the product slurry was used for testing the centrifuge cloth prior to filtration.
Product Analysis:
50:50 Magnesium Omega-3 Salt: Magnesium Phosphate Co-Salt
% Magnesium=9.7%
% EPA+DHA, by GC Analysis, as fatty acid methyl esters (FAMES)=15.3%
Theoretical Expected % EPA+DHA=15.0%
Thermogravimetric Analysis of % Weight Loss on Heating to 120° C.=5.7%
The product is a solid free flowing material.

Working Example D

Preparation of 90:10 Calcium Omega-3 Salt: Calcium Citrate Tetrahydrate Co-Salt
1. Preparation of Mixed Sodium Salt Solution: Assemble a round bottom 2-Liter three-necked flask equipped with a motor-driven Teflon paddle stirrer, a nitrogen purge inlet, a heating mantle, and a 130-mL capacity addition funnel with pressure-equalizing sidearm. Purge thoroughly with nitrogen. Then add 600-mL's degassed deionized water. Continue a slow nitrogen purge throughout the remaining steps.
2. Next add 6.74-grams citric acid.

3. Next, add 84.1 grams of a "free fatty acid" mixture derived from menhaden oil by saponification and having an average equivalent weight of 288 grams/mole.
4. Adjust the temperature of the stirring mixture to 30-32° C. Then add dropwise a solution of 32.0 grams 50% sodium hydroxide dissolved in 100-mL's of degassed deionized water.
5. Cool the solution to <30° C.
6. Exchange Reaction: Next, begin the dropwise addition of 100-mL's of a 21% aqueous solution of calcium chloride. The addition rate is such that about 45-minutes is required for complete addition of the 100-mL's of calcium chloride solution. Precipitation occurs throughout the addition. The final resulting reaction mixture is a thick slurry of white solids.
7. Stir for an additional one hour. Then, shut off the agitator and allow to sit overnight under nitrogen blanket.
8. Collect the product by vacuum filtering the slurry on a 12.5-cm Buchner Funnel, using a Fisherbrand number 6, glass fiber filter medium. Wash the product with 200-mL's degassed deionized water.
9. The wet product was next reslurried in 400-mL's degassed deionized water. Then, it was again collected on a Buchner Funnel employing a Fisherbrand No. 6 glass fiber filter.
10. Dry the wet product in a vacuum oven to constant weight. The theoretical weight of dry product is 100-grams. Actual obtained dry weight is 104-grams.
    Product Analysis:
    90:10 Calcium Omega-3 Salt: Calcium Citrate Co-Salt
    % Calcium=7.0%
    % EPA+DHA, by GC Analysis, as fatty acid methyl esters (FAMES)=24.9%
    Theoretical Expected % [EPA+DHA]=27.0%
    Thermogravimetric Analysis of % Weight Loss on Heating to 120° C.=2.0%
The product is a solid free flowing material.

The working examples A-D use a fish oil that is either 30% or 94% by weight omega-3 fatty acids; they use citrate or phosphate as the co-anion, and calcium or magnesium as the mineral. There were two experiments in which co-salts did not form. In the first, a 50:50 magnesium citrate co-salt was attempted. The procedure gave two distinct salts. It is believed that one factor that may have resulted in the inability to produce a co-salt was the fact that at the temperatures under which the experiment was conducted (i.e., about 30° C.), magnesium citrate stays in solution and the omega-3 citrate precipitates out. It is believed that if the experiment were conducted at a somewhat higher temperature or that if a lower ratio of omega-3 fatty acid were used, that a co-salt would have formed. In the second, a 50:50 calcium citrate co-salt was attempted to be made using a fish oil that was 94% omega-3 fatty acid by weight (that is, the oil had a very high concentration of omega-3 fatty acids). Calcium citrate co-salts did not form when the fatty acid starting material had an omega-3 concentration above about 50%. However, if the starting material is less than 50% omega-3 fatty acid, the calcium citrate co-salt was formed. In fact, as seen in Table 6, calcium citrate co-salts were formed.

Working Example B used a fatty acid starting material that was about 94% fatty acid by weight. Hence, co-salts can be formed using highly concentrated (or very pure) omega-3 fatty acid compositions.

As various changes could be made in the above constructions without departing from the scope of the claimed invention, it is intended that all matter contained in the above description or shown in the accompanying drawings shall be interpreted as illustrative and not in a limiting sense. For example, although the working examples use a fish oil that 35% or 65% omega-3 fatty acids by weight, the starting oil could have an omega-3 content as low as 5% by weight and as high as 100% by weight (i.e., pure omega-3 fatty acid). This example is merely illustrative.

The invention claimed is:

1. A co-salt comprised of at least one polyunsaturated fatty acid anion and at least one co-anion; said co-anion being an anion which is not a fatty acid anion and that is less waxy, less hydrophobic and more structurally rigid than said at least one polyunsaturated fatty acid anion; said co-salt further comprising at least one cation which is ionically bonded with said at least one polyunsaturated fatty acid anion and said at least one co-anion to define a fatty acid salt component of the co-salt and a co-anion salt component of the co-salt; wherein the at least one polyunsaturated fatty acid anion comprises at least one omega-3 fatty acid and/or at least one omega-6 fatty acid;
   said at least one co-anion is chosen from the group consisting of citric acid, lactic acid, phosphoric acid, fumaric acid, malic acid, gluconic acid, acetic acid, ascorbic acid, aspartic acid, sulfuric acid, formic acid, propionic acid, succinic acid, adipic acid, salicyclic acid, benzoic acid, phthalic acid, maleic acid, malonic acid, pyruvic acid, sorbic acid, caprylic acid, glutaric acid, pimelic acid, glucoheptanoic acid, glycerophosphoric acid, glutamic acid, glutathione, lecithin, phenylalanine, valine, leucine, isoleucine, threonine, methionine, lysine, arginine, histidine and combinations thereof;
   said at least one cation being chosen from the group consisting of calcium, magnesium, zinc, iron, manganese, copper, potassium, sodium, ammonium, and combinations thereof; and
   the weight ratio of the fatty acid anion to the non-fatty acid co-anion in the co-salt ranges from about 90:10 to about 10:90.

2. The co-salt of claim 1 wherein the co-salt has at least one of an infrared spectrum and an x-ray diffraction pattern in which characteristic modes for the co-salt are off-set from corresponding characteristic modes for an admixture of the fatty acid salt and co-anion salt of the co-salt.

3. The co-salt of claim 1 wherein the at least one cation for the co-salt is chosen from the group consisting of calcium, magnesium, zinc, iron and combinations thereof.

4. The co-salt of claim 1 wherein the co-anion is chosen from the group consisting of citric acid, lactic acid, phosphoric acid, fumaric acid, sulfuric acid, and combinations thereof.

5. The co-salt of claim 1 wherein said fatty acid anion is at least 5% by weight omega-3 or omega-6 fatty acids.

6. The co-salt of claim 5 wherein the omega-3 fatty acid content of the fatty acid anion varies from 15% to 95% by weight.

7. The co-salt of claim 1 wherein said at least one omega-3 fatty acid is chosen from the group consisting of alpha-linolenic acid (C18:3, n-3), eicosatetraenoic acid (C20:4, n-3), moroctic acid (C18:4, n-3), eicosapentaenoic acid (EPA) (C20:5, n-3), heneicosapentaenoic acid (C21:5, n-3), docosapentaenoic acid (C22:5, n-3), and docosahexaenoic acid (DHA) (C22:6, n-3), and combinations thereof; and wherein the omega-6 fatty acid is chosen from the group consisting of linoleic acid 18:2 (n-6), eicosatrienoic acid (C20:3, n-6), arachidonic acid 20:4 (n-6), and combinations thereof.

8. The co-salt of claim 1 wherein the fatty acid anion comprises a complex mixture of multiple omega fatty acid anions and non-omega fatty acid anions.

9. The co-salt of claim 8 wherein said complex mixture of fatty acids is derived from:

(a) fish oils, seed oils, or microbial oils, or
(b) esters of fish oils, seed oils, or microbial oils, or
(c) triglycerides resulting from the re-esterification of purified esters from fish oils, seed oils, microbial oils.

10. The co-salt of claim 1 wherein the composition is about 40% by weight to about 80% by weight fatty acid anion and about 60% by weight to about 20% by weight co-anion.

11. The co-salt of claim 1 wherein the co-anion is carbonic acid.

12. A co-salt comprised of a fatty acid salt component, comprising at least one fatty acid anion and a non-fatty acid salt component, comprising at least one non-fatty acid co-anion; the co-salt being granular and free flowing; the co-salt having at least one of an infrared spectra and an X-ray diffraction pattern in which characteristic modes for the co-salt are off-set from corresponding characteristic modes for an admixture of the fatty acid salt and co-anion salt of the co-salt; wherein the fatty acid anion comprises at least one omega-3 fatty acid and/or at least one omega-6 fatty acid; and said at least one co-anion is chosen from the group consisting of citric acid, lactic acid, phosphoric acid, fumaric acid, malic acid, gluconic acid, acetic acid, ascorbic acid, aspartic acid, sulfuric acid, formic acid, propionic acid, succinic acid, adipic acid, salicyclic acid, benzoic acid, phthalic acid, maleic acid, malonic acid, pyruvic acid, sorbic acid, caprylic acid, glutaric acid, pimelic acid, glucoheptanoic acid, glycerophosphoric acid, glutamic acid, glutathione, lecithin, phenylalanine, valine, leucine, isoleucine, threonine, methionine, lysine, arginine, histidine and combinations thereof; and at least one cation ionically bonded with the fatty acid anion and the non-fatty acid co-anion.

13. The co-salt of claim 12 wherein the weight ratio of the fatty acid anion to the non-fatty acid co-anion in the co-salt ranges from about 90:10 to about 10:90.

14. The co-salt of claim 12 wherein the fatty acid has an omega-3 fatty acid content of up to 95% by weight.

15. The co-salt of claim 12 wherein the omega-3 fatty acid is selected from the group consisting of alpha-linolenic acid, moroctic acid, eicosatetraenoic acid, eicosapentaenoic acid (EPA), heneicosapentaenoic acid, docosapentaenoic acid, docosahexaenoic acid (DHA), and combinations thereof.

16. The co-salt of claim 12 wherein the cation being selected from the group consisting of Ca, Mg, Cu, Zn, Fe, Mn, K, Na, $NH_4$ and combinations thereof.

17. The co-salt of claim 12 in which the weight ratio of the fatty acid anion to the non-fatty acid co-anion ranges from about 50:50 to 70:30, and wherein the cation for the salts is calcium or magnesium, the omega-3 fatty acid content comprises about 15-47% of the weight of the co-salt, and the non-fatty acid salt is citrate or phosphate.

18. The co-salt of claim 17 in which the fatty acid component is derived from fish oil.

19. The co-salt of claim 18 wherein the fatty acid is 18% by weight EPA and 12% by weight DHA.

20. The co-salt of claim 12 wherein the co-anion is carbonic acid.

* * * * *